United States Patent [19]

Edwards

[11] 4,188,385
[45] Feb. 12, 1980

[54] THIOETIANIC ACID DERIVATIVES

[75] Inventor: John A. Edwards, Los Altos, Calif.

[73] Assignee: Syntex (U.S.A.) Inc., Palo Alto, Calif.

[21] Appl. No.: 893,388

[22] Filed: Apr. 5, 1978

[51] Int. Cl.$^2$ .................... A61K 31/58; C07J 71/00
[52] U.S. Cl. .................... 424/241; 260/239.55 D; 424/243
[58] Field of Search .................... 260/239.55 D, 397.1

[56] References Cited

U.S. PATENT DOCUMENTS

| | | | |
|---|---|---|---|
| 3,856,828 | 12/1974 | Phillipps et al. | 260/397.1 |
| 3,989,686 | 11/1976 | Phillipps et al. | 260/397.1 |

*Primary Examiner*—Elbert L. Roberts
*Attorney, Agent, or Firm*—Tom M. Moran; Gerard A. Blaufarb

[57] ABSTRACT

Certain 3-oxoandrost-4-ene and 3-oxoandrosta-1,4-diene 17 beta-thiocarboxylic acid esters are useful as antiinflammatory steroids. These compounds are optionally substituted at the 6 alpha-position with fluoro, or chloro; optionally substituted at the 9 alpha position with fluoro, chloro or bromo; substituted at the 11 position with a keto, a beta-hydroxy on a beta-chloro (the latter only when there is a 9 alpha-chloro); substituted at 16 alpha, 17 alpha-positions with isopropylidenedioxy; and substituted at 16 alpha (or 16 beta) with methyl or hydrogen when there is a 17 alpha-hydroxy (or an ester).

41 Claims, No Drawings

THIOETIANIC ACID DERIVATIVES

BACKGROUND OF THE INVENTION

1. Field of the Invention

This invention relates to novel derivatives of alkyl, phenyl or benzyl 3-oxoandrost-4-ene-17 beta-thiocarboxylates and the corresponding androsta-1,4-dienes. More specifically, it relates to 16 alpha, 17 alpha-acetonides and 17 alpha-hydroxy-16-methyl compounds which are optionally substituted at the 6 alpha-position with fluoro or chloro and at the 9 alpha-position with fluoro, chloro or bromo, and are substituted at the 11-position with betahydroxy, beta-chloro (when there is a 9 alpha-chloro) or a keto. The 17 beta-thiocarboxylates are active anti-inflammatory agents in mammals. The invention further relates to pharmaceutically active compositions comprising a selected 17 beta-thiocarboxylate of the invention in combination with pharmaceutically acceptable excipient. This invention even further relates to a process for the preparation of these novel compounds.

2. Prior Art

Certain 3-oxoandrost-4-ene 17 beta-carboxylic acids which are substituted at the 9 position with chlorine or fluorine and at the 11 position with keto or hydroxy or chloro group are known. See for example U.S. Pat. Nos. 3,828,080 and 3,981,894 both assigned to Glaxo. It is also known that 3-oxoandrost-4-ene 17 beta-carboxylic acids may be substituted at both the 9 alpha and 6 alpha positions with fluoros. See for example U.S. Pat. No. 3,636,010.

It is also known from U.S. Pat. No. 3,989,686 to Phillips et al of Glaxo that steroids of formula (II)

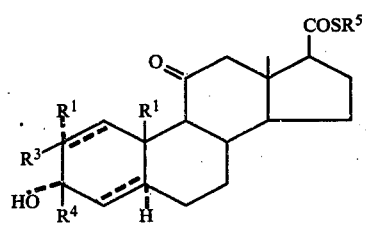

wherein
$R^1$ is H or $CH_3$;
$R^2$ is H or $CH_3$;
$R^3$ is H or, when $R^2$ is H, $C_{1-6}$ alkoxy, $C_{1-5}$ alkyl, thiocyanato or halogen;
$R^4$ is H or $CH_3$;
$R^5$ is $C_{1-6}$ alkyl optionally substituted by halo or $NR^6R^7$, where $R^6$ and $R^7$ are the same or different $C_{1-6}$ alkyl or $R^6$ and $R^7$ together with N are morpholino, thiamorpholine or morpholino substituted with $C_{1-6}$ alkyl; and
the dotted line in the "A" ring represents an optional double bond at these positions. These compounds are useful as anesthetics.

Methyl 3 beta-acetoxyallothiolcholonate and methyl 3 beta-acetoxy-etiothiochol-5-enate are also known. See, e.g., Jerger et al, Helv. Chem. Acta. 29, 684–92 (1947).

A heretofore unknown series of 3-oxoandrost-4-ene 17 beta-thiocarboxylates and derivatives thereof has been discovered and is disclosed herein. The 17 beta-thiocarboxylates exhibit topical anti-inflammatory activity and few adverse side effects.

SUMMARY OF THE INVENTION

One aspect of this invention is a compound chosen from those represented by the formula (I)

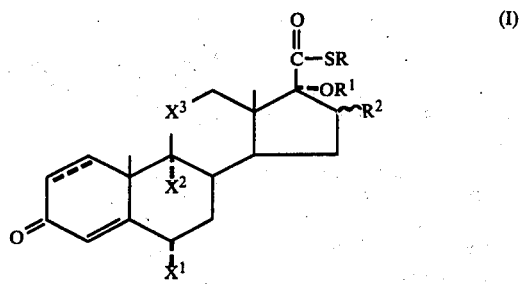

wherein
$X^1$ is hydrogen, fluoro, or chloro;
$X^2$ is hydrogen, fluoro, chloro or bromo;
$X^2$ is =C=O or

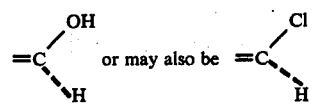

when $X^2$ is chloro;

R is alkyl of 1 through 6 carbon atoms, or phenyl or benzyl optionally substituted with a substituent which is alkyl of 1 through 4 carbon atoms, alkoxy of 1 through 4 carbon atoms or halo;

$R^1$ is hydrogen or alkanoyl of 2 through 6 carbon atoms when $R^2$ is hydrogen, alpha-methyl or beta-methyl or $OR^1$ and $R^2$ together are 16 alpha, 17 alpha-isopropylidenedioxy; and the bond between C-1 and C-2 is a double or single bond.

Another aspect of this invention is an anti-inflammatory pharmaceutical composition which comprises a suitable pharmaceutical excipient in combination with an effective amount of a suitable compound chosen from those represented by Formula (I), above, wherein each of the substituents are as defined. Particularly valuable compounds in this composition are set forth hereafter.

Still another aspect of this invention is a method for treating an inflamed condition in mammals which comprises treating the afflicted mammal with an effective amount of a suitable compound chosen from those represented by formula (I), above, wherein substituents are as defined above.

Still another aspect of this invention is a process for preparing a compound of this invention which process comprises treating a corresponding reactive derivative of a 17 beta-carboxylic acid with an alkali metal salt of an appropriate alkyl, phenyl or benzyl sulfide (RSH).

DETAILED DESCRIPTION AND PREFERRED EMBODIMENTS

Compounds

In its broadest aspect, this invention is a compound chosen from those represented by formula (I) wherein
$X^1$ is hydrogen, fluoro or chloro;
$X^2$ is hydrogen, fluoro, chloro or bromo;
$X^3$ is =C=O or

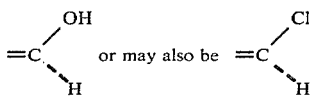

when X² is chloro;

R is alkyl of 1 through 6 carbon atom, or is phenyl or benzyl optionally substituted with alkyl of 1 through 4 carbon atoms, alkoxy of 1 through 4 carbon atoms or halo;

R¹ is hydrogen or alkanoyl of 2 through 6 carbon atoms when R² is hydrogen, alpha-methyl or beta-methyl or OR¹ and R² together are 16 alpha, 17 alpha-isopropylidenedioxy; and the bond between C-1 and C-2 is a double or single bond.

One subgroup of the broad aspect of this invention includes the compounds represented by formula (I) wherein R is alkyl of 1-6 carbon atoms, benzyl or phenyl (preferably methyl or ethyl); OR¹ and R² together are 16 alpha, 17 alpha-isopropylidenedioxy; X¹ is fluoro; X² is hydrogen, fluoro or chloro; and X³ is

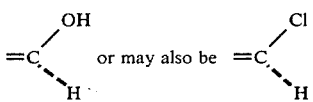

when X² is chloro. Of this subgroup the compounds wherein R is methyl and X² is fluoro or chloro are preferred.

Another subgroup of the broad aspect of the invention comprises those compounds represented by the formula (I) wherein R² is alpha-methyl.

Still another subgroup are those wherein R² is alpha-methyl, R¹ is alkanoyl of 2-6 carbon atoms; R is alkyl of 1-6 carbon atoms, benzyl or phenyl; X¹ is fluoro or hydrogen (especially the former) X² is hydrogen, fluoro or chloro; and X³ is

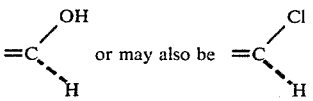

when X² is chloro. Of this subgroup, those compounds of formula (I) wherein R is alkyl of 1-2 carbon atoms are preferred, and those particularly preferred, are those wherein R is methyl; X² is fluoro or chloro; and X³ is

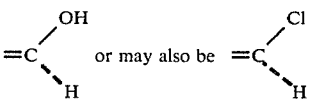

when X² is chloro. The most preferred compounds of this subgroup are those wherein R is methyl, X¹ and X² are fluoro and X³ is

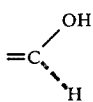

and those wherein R is methyl, X¹ is fluoro, X² is chloro and X² is

In defining the compounds of this invention the term "alkyl" includes both straight chain and branched alkyl groups, thus "alkyl" of 1-6 carbons include methyl, ethyl, n-propyl, isopropyl, n-butyl, isobutyl, t-butyl, pentyl, isoamyl, n-hexyl and the like. The phenyl and benzyl substituents may be substituted on the phenyl ring at the 2, 3 or 4-positions with one substituent such as alkoxy (e.g. methoxy, ethoxy, n-propoxy, t-butoxy and the like), alkyl of 1-4 carbons (e.g. methyl, ethyl, isopropyl, n-propyl, t-butyl, n-butyl, etc.), or a halo such as fluoro, chloro, bromo or iodo. Preferably the substitution is at the 2 or 4 positions.

The term "alkanoyl" refers to a radical of the formula

wherein R⁴ is alkyl of 1-5 carbon atoms and includes, e.g., acetyl, propionyl, butyryl, valeryl, caproyl and the like.

In naming the compounds of this invention the substituents present on the androstane ring shall be included alphabetically and the compounds shall be alkyl (or phenyl or benzyl) 17 beta-carboxylates. For example, if in formula (I), above, X¹ is fluoro, X² is chloro, X³ is

R is methyl, R¹ is acetoxy and R² is alpha-methyl the name is methyl 17 alpha-acetoxy-9 alpha, 11 beta-dichloro-6 alpha-fluoro-16 alpha-methyl-3-oxoandrosta-1,4-diene-17 beta-thiocarboxylate. If on the other hand, R is hydrogen but X¹, X², X³, X⁴, R¹ and R² are the same, the compound is named 17 alphaacetoxy-9 alpha, 11 beta-dichloro-6 alpha-fluoro-16 alphamethyl-3-oxoandrosta-1,4-diene 17 beta-thiocarboxylic acid.

Compound Preparation

The compounds of the invention may be prepared by any convenient method, and in most cases, they can be prepared by conventional techniques. They may, for example, be prepared by reacting a reactive derivatives of an appropriate androsta-1,4-diene 17 beta-carboxylic acid (or the corresponding 4-ene), with an excess (e.g. about 1.1 to 5 molar equivalents based on the steroid) of alkali metal salt of a compound of the formula RSH where R is alkyl, benzyl or phenyl as defined hereinbefore. Representative alkali metal salts include, e.g., sodium methyl sulfide, sodium ethyl sulfide, sodium benzyl sulfide, sodium phenyl sulfide, potassium methyl sulfide, and the like. The alkali metal salt can be reacted directly with the reactive derivative of the 17 beta-carboxylic acid, or the salt can be formed in situ by mixing an alkali metal hydride, such as sodium hydride or potassium hydride, with an alkyl, phenyl or benzyl sulfide. The thioesterification reaction readily takes place at temperatures of about 10° to 100° C. (preferably at ambient temperatures of about 20°–25° C.) in a suitable inert solvent such as dimethylformamide, diethylformamide, dimethylacetamide, and the like. The reactive derivative of the 17 beta-carboxylic acid may be an acid chloride, but is preferably a mixed anhydride, such as the dialkyl phosphate ester prepared by reacting a dialkyl (1-4 carbons) chlorophosphate (e.g. diethyl chlorophosphate) with the appropriate 17 beta-carboxylic acid in an inert solvent such as tetrahydrofuran (THF) under an inert atmosphere (nitrogen).

The 17 beta-carboxylic acid starting materials are prepared by eliminating the 21 carbon atom from a suitable 21-hydroxy-3,20-dioxopregn-4-ene or pregna-1,4-diene. This is readily accomplished by any means known in the art such as using sodium hypobromite as taught in U.S. Pat. No. 2,769,822 or using sodium periodate. Preferably, however, the elimination of the 21 carbon atom is carried out by using an alkali metal carbonate in alcohol and the presence of oxygen as described in PA-880, filed even date herewith. In the latter case the reaction is carried out at room temperature and atmospheric pressure while the source of oxygen is preferably air. Generally the reaction will be completed within less than 24 hours with a constant stream of air being bubbled into a stirred reaction mixture.

Suitable 21-hydroxy-3,20-dioxopregn-4-enes or -pregna-1,4-dienes include known compounds such as corticosterone, hydrocortisone, prednisolone, betamethasone, dexamethasone, triamcinolone, paramethasone, fluocinolone, triamcinolone acetonide, fluocinolone acetonide, and the like. By following procedures generally known in the art steroids of a relatively simple structure can be converted to other structures as desired.

For example, the 6-fluoro starting steroids can be prepared from known steroids such as 17 alpha-hydroxyprogesterone or hydrocortisone. The 6-fluoro group can be introduced by treating a 3-methoxy-pregna-3,5-diene (prepared by reacting a 3-keto-pregn-4-ene with triethyl orthoformate in methanol) with perchloryl fluoride in acetone-water 9:1.

Other 6-fluoro starting steroids employed in the present process to prepare the novel 17 beta-thiocarboxylic acid derivatives of this invention are described in the literature and in United States and foreign patents. For example, see U.S. Pat. Nos. 2,983,737, 2,983,739, 3,053,838, 3,057,858, 3,124,251, 3,126,375, 3,201,391 and 3,248,389.

The 9 alpha-fluoro, chloro or bromo group is introduced by treating a 9 beta, 11 beta-oxido steroid with hydrogen fluoride, hydrogen chloride or hydrogen bromide respectively in an inert, nonaqueous, preferably anhydrous, solvent or mixture of such solvents. For example, see U.S. Pat. No. 3,211,758 to Tarkoey wherein a hydrogen fluoride/urea complex is employed. The 9 beta, 11 beta-oxido steroid is prepared from the corresponding pregna-4,9(11) -diene (which is prepared by treating the corresponding 11 beta-hydroxy steroid with methane sulfonyl chloride in diemthylformamide in the presence of pyridine and a catalytic amount of sulfur trioxide) by treating the pregna-4,9(11)-diene with N-bromoacetamide and perchloric acid in dioxane or tetrahydrofuran, and then refluxing the resulting 9-bromo-11-hydroxy steroid with potassium acetate in acetone. The 9 alpha, 11 beta-dichloro groups are introduced by treating the corresponding pregna-4,9(11)-diene with chlorine gas in chloroform.

A 16-methyl group is introduced by treating the corresponding 20-keto-pregn-16-ene with methyl magnesium bromide in the presence of cuprous chloride in an ether such as tetrahydrofuran. The 20-keto-pregn-16-ene is prepared by preparing the 3,20-bis-semicarbazone of a 3,20-diketo-17 alpha-hydroxy steroid, treating the semicarbazone with glacial acetic acid and acetic anhydride and then allowing the resulting product to react with aqueous pyruvic acid.

The 17 alpha-hydroxy group is introduced in conjunction with the 16 beta-methyl group by first treating the corresponding 16-methyl-pregn-16-ene (which is prepared by treating the corresponding pregn-16-ene with diazomethane and then heating the resulting product to 180° C.) with hydrogen peroxide, in an aqueous basic media, then permitting the resulting 16,17-oxido-16-methyl steroid to react with hydrogen bromide in glacial acetic acid. The resulting 16,17-bromohydrin is hydrogenated with the use of a palladium catalyst to afford the corresponding 16 betamethyl-17 alpha-hydroxy derivative.

The 17 alpha-hydroxy group is introduced in conjunction with the 16 alpha-methyl by methods known in the art, such as the method described by Edwards et al in the Journal of the American Chemical Society 82, 2318–22, 1960. In this process an appropriate 21-substituted 16 alpha-methylpregna-1,4-diene-3,2-dione is converted to 20-enol acetate by refluxing with acetic anhydride and freshly distilled acetyl chloride. The 20-enol acetate is recovered and reacted with monoperphthalic acid in ether and benzene to form the 17,20-epoxide which in turn is treated with methanol and aqueous potassium hydroxide to give the 16 alpha-methyl-17 alpha-hydroxy steroid which is isolated by means known in the art.

Administration and Formulation

The compounds of this invention are useful for the relief of inflamed conditions in mammals, and more specifically are useful for relieving inflammatory manifestations of corticosteroid responsive dermatoses. Initial approximation of anti-inflammatory activity is done by the following procedure of McKenzie, S. W. and Stoughton, R. B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of the novel steroids of this invention, that is an amount which results in improvement of the inflamed conditions. Preferably the steroids are first formulated to prepare a suitable pharmaceutical formulation, as discussed hereinafter, which is then placed in contact with the afflicted area. An effective amount will depend upon the particular condition and the animal receiving the treatment but will vary between 0.001% to 10% by weight of the pharmaceutical composition and preferably will be between 0.02 and 1% by weight of the formulation. Using these levels in the formulation, a therapeutically effective and non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the animal's system.

The novel steroids of this invention may be formulated with suitable pharmaceutical excipients known in the art to form particularly effective anti-inflammatory compositions which may be administered orally, nasally, rectally or, preferably, topically. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| Water/glycol mixture (15% or more glycol) | 50–99 parts by weight |
|---|---|
| Fatty alcohol | 1–20 |
| Non-ionic Surfactant | 0–10 |
| Mineral oil | 0–10 |
| Typical pharmaceutical adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| White petrolatum | 40–94 parts by weight |
|---|---|
| Mineral Oil | 5–20 |
| Glycol solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001–10.0 parts by weight |
|---|---|
| Propylene Carbonate | 1–10 |
| Solvent | 1–10 |
| Surfactant | 1–10 |
| White Petrolatum | 70–97 | surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| Glycol solvent | 50–35 parts by weight |
|---|---|
| Fatty alcohol | 15–45 |
| Compatible plasticizer | 0–15 |
| Compatible coupling Agent | 0–15 |
| Penetrant | 0–20 |
| Active Ingredients | 0.001–10.0 |

Preparation 1

A process is set forth for preparing 16 alpha-methyl-3-oxoandrosta-1,4-diene 17 beta-carboxylic acids substituted at the 9 alpha-position with hydrogen, fluoro, chloro or bromo; at the 6 alpha-position with hydrogen, fluoro or chloro; and at the 11 beta-position with hydroxy or chloro when 9 alphais chloro substituted.

A. Preparation of 6 alpha,9 alpha-difluoro-11 beta, 17 alpha-dihydroxy-16 alpha-methyl-3-oxoandrosta-1,4-diene 17 beta-carboxylic acid.

Thirty-five grams of flumethasone is mixed with 550 ml of methanol and 35 g of anhydrous potassium carbonate and stirred at room temperature and atmospheric pressure while a current of air is slowly bubbled through the solution for 22 hours. Methanol is added at intervals to maintain a constant volume. The reaction mixture is diluted with water to 1.5 l, then concentrated hydrochloric acid is added slowly to the mixture under magnetic stirring until a final pH of 2 is obtained. Methanol is eliminated under reduced pressure, and the resulting crystalline precipitate is collected by filtration, washed with water, and air dried to give 6 alpha,9 alpha-difluoro-11 beta,17 alpha-dihydroxy-16 alpha-methyl-3-oxoandrosta-1,4-diene-17 beta-carboxylic acid, melting point (m.p.) 289.5°–290° C.

B. By following the procedure set forth in part A of this example but substituting other appropriate starting materials the following compounds of this invention can be prepared:

9 alpha, 11 beta-dichloro-6 alpha-fluoro-17 alpha-hydroxy-16 alpha-methyl-3-oxoandrosta-1,4-diene 17 beta-carboxylic acid;

9 alpha-chloro-6 alpha-fluoro-11 beta,17 alpha-dihydroxy-16 alpha-methyl-3-oxo-androsta-1,4-diene 17 beta-carboxylic acid;

9 alpha-bromo-6 alpha-fluoro-11 beta,17 alpha-dihydroxy-16 alpha-methyl-3-oxo-androsta-1,4-diene 17 beta-carboxylic acid;

9 alpha, 11 beta-dichloro-17 alpha-dihydroxy-16 alpha-methyl-3-oxo-androsta-1,4-diene 17 beta-carboxylic acid;

11 beta,17 alpha-dihydroxy-16 alpha-methyl-3-oxo-androsta-1,4-diene 17 beta-carboxylic acid;

9 alpha-chloro-11 beta,17 alpha-dihydroxy-16 alpha-methyl-3-oxo-androsta-1,4-diene 17 beta-carboxylic acid;

9 alpha-bromo-11 beta,17 alpha-dihydroxy-16 alpha-methyl-3-oxo-androsta-1,4-diene 17 beta-carboxylic acid;

9 alpha-fluoro-11 beta,17 alpha-dihydroxy-16 alpha-methyl-3-oxo-androsta-1,4-diene 17 beta-carboxylic acid;

6 alpha-fluoro-11 beta,17 alpha-dihydroxy-16 alpha-methyl-3-oxo-androsta-1,4-diene 17 beta-carboxylic acid;

6 alpha,9 alpha-dichloro-11 beta,17 alpha-dihydroxy-16 alpha-methyl-3-oxoandrosta-1,4-diene 17 beta-carboxylic acid;

6 alpha-chloro,9 alpha-fluoro-11 beta,17 alpha-dihydroxy-16 alpha-methyl-3-oxo-androsta-1,4-diene 17 beta-carboxylic acid;

9 alpha-bromo-6 alpha-chloro-11 beta,17 alpha-dihydroxy-16 alpha-methyl-3-oxo-androsta-1,4-diene 17 beta-carboxylic acid;

6 alpha-chloro-11 beta,17 alpha-dihydroxy-16 alpha-methyl-3-oxoandrosta-1,4-diene 17 beta-carboxylic acid; and 6 alpha,9 alpha-dichloro-11 beta,17 alpha-dihydroxy-16 alpha-methyl-3-oxo-androsta-1,4-diene 17 beta-carboxylic acid.

C. By following in principle the process of Part A but substituting other appropriate starting materials having a 17 beta-methyl group or being unsubstituted at 17 (e.g. beta-methasone or hydrocortisone), other 17 beta-methyl or 17-unsubstituted starting materials are prepared.

D. Ten g of a compound prepared according to Parts A–C of this preparation is dissolved in 100 ml methanol. Fifty ml of anhydrous pyridine and 25 ml of propionic anhydride are added and the resulting mixture stirred until TLC shows the reaction is complete. The solution is cooled in an ice-water bath and slowly diluted with water up to 2 l. The resulting crystalline precipitate is collected by filtration and air dried to give the 17 alpha-propionate. Other alkanoates are obtained by substituting other anhydrides for propionic anhydride.

Preparation 2

A process is set forth for preparing 16 alpha,17 alpha-isopropylidenedioxy-3-oxoandrosta-1,4-diene 17 beta-carboxylic acid substituted at 9 alpha with hydrogen, fluoro, chloro or bromo; at 6 alpha with hydrogen, fluoro or chloro; and at 11 beta with hydroxy or chloro when there is a 9 alpha-chloro.

A. By following in principle the process of Preparation 1, Part A but substituting fluocinolone acetonide for flumethasone, one obtains 6 alpha,9 alpha-difluoro-11 beta-hydroxy-16 alpha,17 alpha-isopropylidenedioxy-3-oxoandrosta-1,4-diene 17 beta-carboxylic acid, m.p. 297°–300° C. (with decomposition).

B. By following in principle the process of Part A of this preparation but substituting other 16 alpha,17 alpha-isopropylidenedioxypregna-1,4-diene-3,20-diones for fluocinolone acetonide, other 17 beta-carboxylic acids are obtained, for example 9 alpha,11 beta-dichloro-6 alpha-fluoro-16 alpha,17 alpha-isopropylidenedioxy-3-oxoandrosta-1,4-diene 17 beta-carboxylic acid;

9 alpha-chloro-6 alpha-fluoro-11 beta-hydroxy-16 alpha,17 alpha-isopropylidenedioxy-3-oxoandrosta-1,4-diene 17 beta-carboxylic acid;

6 alpha,9 alpha,11 beta-trichloro-16 alpha,17 alpha-isopropylidenedioxy-3-oxoandrosta-1,4-diene 17 beta-carboxylic acid; and the like.

Specific embodiments of the process of this invention are found in the following Examples which are given by way of illustration only and are not to be interpreted as limiting the scope of the claims appended hereto.

EXAMPLE 1

A process is set forth for preparing alkyl, benzyl or phenyl 17 alpha-alkanoyloxy-16 alpha-methyl-3-oxoandrosta-1,4-diene 17 beta-thiocarboxylates of this invention which are substituted with hydrogen, fluoro or chloro at the 6 alpha-position; with fluoro, chloro, bromo or hydrogen at the 9 alpha-position; and 11 beta-hydroxy or 11 beta-chloro when there is a chloro at 9 alpha.

A. Preparation of methyl 6 alpha,9 alpha-difluoro-11 beta-hydroxy-16 alpha-methyl-3-oxo-17-propionyloxyandrosta-1,4-diene 17 beta-thiocarboxylate.

Six hundred (600) mg of 6 alpha,9 alpha-difluoro-11 beta-hydroxy-16 alpha-methyl-3-oxo-17-propionyloxyandrosta-1,4-diene 17 beta-carboxylic acid, prepared in the manner set forth in Preparation 1,A, are mixed with 8 ml THF and 0.2 ml triethylamine (TEA) in a suitable reaction vessel and stirred at room temperature under $N_2$. Thereafter, 0.24 g of diethyl chlorophosphate (DCP: $(C_2H_5O)_2P(O)Cl$) in 8 ml THF is added over 13 minutes. Stirring is continued for about 6 hours (pH 6). Then, 0.04 ml TEA is added followed by 0.05 gm DCP in 3 ml THF. Stirring is continued for another 17.5 hours. The resulting precipitate is filtered, washed with 10 ml THF and the filtrates are combined. To the filtrate are then added 2.05 ml of a solution prepared previously which consists of 20 ml dimethylformamide (DMF), 0.758 g 75% sodium hydride and 0.86 g (1 ml) methylsulfide. The resulting reaction mixture of the filtrates and the DMF solution is stirred for about 5.5 hours whereupon an additional 1 ml of the DMF solution is added and stirring is continued for another 1.5 hours.

The reaction mixture is then poured into 200 ml of ethyl acetate (EtOAc) which, in turn, is washed twice with 200 ml portions of water, washed with brine, dried for about 15 hours over sodium sulfate and filtered. The solvents are then removed under reduced pressure using a rotary evaporator to give 235 mg of residue which is recrystallized from acetone/hexane to give 54.3 mg of methyl 6 alpha,9 alpha-difluoro-11 beta-hydroxy-16 alpha-methyl-17 alpha-propionyloxyandrosta-1,4-diene 17 beta-thiocarboxylate, m.p. 305°–308° C. (with decomposition).

B. By following in principle the procedure of Part A of this example but substituting other sulfides such as ethyl sulfide, isopropyl sulfide, n-butyl sulfide, phenyl sulfide, or benzyl sulfide for methyl sulfide other compounds of this invention are prepared, namely ethyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 300° C. (with decomposition);

isopropyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 286°–289° C.;

n-butyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 247°–250° C.;

phenyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 281°–283° C. (with decomposition);

benzyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 246°–248° C.

C. By following in principle the process of Part A of this example, but substituting other appropriate steroids for 6 alpha,9 alpha-difluoro-11 beta-hydroxy-16 alpha-methyl-3-oxo-17-propionyloxyandrosta-1,4-diene 17 beta-carboxylic acid and other appropriate alkyl, phenyl or benzyl sulfides for methyl sulfide, other compounds of this invention are obtained such as methyl 9 alpha,11 beta-dichloro-6 alpha-fluoro-16 alpha-methyl-3-oxo-17 alpha-propionyloxyandrosta-1,4-diene 17 beta-thiocarboxylate;

methyl 9 alpha-chloro-6 alpha-fluoro-11 beta-hydroxy-16 alpha-methyl-3-oxo-17 alpha-propionyloxyandrosta-1,4-diene 17 beta-thiocarboxylate;

ethyl 9 alpha-bromo-6 alpha-fluoro-11 beta-hydroxy-16 alpha-methyl-3-oxo-17 alpha-propionyloxyandrosta-1,4-diene 17 beta-thiocarboxylate;

methyl 17 alpha-acetoxy 9 alpha,11 beta-dichloro-16 alpha-methyl-3-oxoandrosta-1,4-diene 17 beta-thiocarboxylate;

methyl 11 beta-hydroxy-16 alpha-methyl-3-oxo-17 alpha-propionyloxyandrosta-1,4-diene 17 beta-thiocarboxylate;

isopropyl 17 alpha-acetoxy-9 alpha-chloro-11 beta-hydroxy-16 alpha-methyl-3-oxoandrosta-1,4-diene 17 beta-thiocarboxylate;

methyl-17 alpha-butyryloxy-9 alpha-fluoro-11 beta-hydroxy-16 alpha-methyl-3-oxoandrosta-1,4-diene 17 beta-thiocarboxylate;

methyl 6 alpha-fluoro-11 beta-hydroxy-16 alpha-methyl-3-oxo-17 alpha-propionyloxyandrosta-1,4-diene 17 beta-thiocarboxylate;

methyl 6 alpha-chloro,9 alpha-fluoro-11 beta-hydroxy-16 alpha-methyl-3-oxo-17 alpha-propionyloxyandrosta-1,4-diene 17 beta-thiocarboxylate.

EXAMPLE 2

A process is set forth for preparing alkyl, benzyl or phenyl 17 alpha-hydroxy-16 alpha-methyl-3-oxoandrosta-1,4-diene 17 beta-thiocarboxylates of this invention which are substituted at the 6 alpha-position with fluoro, chloro or hydrogen; at the 9 alpha-position with hydrogen, fluoro, chloro or bromo; and at the 11 beta-position with hydroxy or also chloro when there is a 9 alpha-chloro.

A. Preparation of ethyl 6 alpha,9 alpha-difluoro-11 beta,17 alpha-dihydroxy-16 alpha-methyl-3-oxoandrosta-1,4-diene 17 beta-thiocarboxylate.

One hundred five (105) mg of 6 alpha,9 alpha-difluoro-11 beta,17 alpha-dihydroxy-16 alpha-methyl-3-oxoandrosta-1,4-diene 17 beta-carboxylic acid are dissolved in 7 ml DMF and cooled to −10° C. Eighty (80) mg carbonyl diimidazole (CDI) are dissolved in 30 ml DMF, and this solution is added to the DMF/acid solution under a nitrogen blanket. The resulting mixture is stirred for about 18 hours at −5° C., and about 0.2 ml ethyl sulfide (EtSH) is added thereto. The reaction is stirred at −5° C. for an additional 16 hours. The reaction mixture is stored in the freezer for 2 weeks, the solvents removed under reduced pressure.

The residue is applied to a 1 meter×0.75 TLC plate and developed twice with a mixture of 10% acetone/90% benzene. After recovery, the material is recrystallized from acetone/hexane to give 47 mg of ethyl 6 alpha,9 alpha-difluoro-11 beta,17 alpha-dihydroxy-16 alpha-methyl-3-oxoandrosta-1,4-diene 17 beta-thiocarboxylate, m.p. 235°–239° C. (with decomposition).

B. Similarly, by following in principle the process of Part A of this example but substituting other alkyl, phenyl or benzyl sulfides for ethyl sulfide, other compounds of this invention such as methyl 6 alpha,9 alpha-difluoro-11 beta,17 alpha-dihydroxy-16 alpha-methyl-3-oxoandrosta-1,4-diene 17 beta-thiocarboxylate;

n-hexyl 6 alpha,9 alpha-difluoro-11 beta,17 alpha-dihydroxy-16 alpha-methyl-3-oxoandrosta-1,4-diene 17 beta-thiocarboxylate;

phenyl 6 alpha,9 alpha-difluoro-11 beta,17 alpha-dihydroxy-16 alpha-methyl-3-oxoandrosta-1,4-diene 17 beta-thiocarboxylate;

benzyl 6 alpha,9 alpha-difluoro-11 beta,17 alpha-dihydroxy-16 alpha-methyl-3-oxoandrosta-1,4-diene 17 beta-thiocarboxylate; and the like.

C. Similarly, by following in principle the process of Part A or Part B but substituting other appropriate 17 beta-carboxylic acid prepared in the manner set forth in Preparation 1 for 6 alpha,9 alpha-difluoro-11 beta,17 alpha-dihydroxy-16 alpha-methyl-3-oxoandrosta-1,4-diene 17 beta-carboxylic acid, other compounds of this invention are obtained such as methyl 6 alpha-fluoro-11 beta,17 alpha-dihydroxy-16 alpha-methyl-3-oxoandrosta-1,4-diene 17 beta-thiocarboxylate;

methyl 9 alpha-fluoro-11 beta,17 alpha-dihydroxy-16 alpha-methyl-3-oxoandrosta-1,4-diene 17 beta-thiocarboxylate;

methyl 6 alpha-fluoro-9 alpha,11 beta-dichloro-17 alpha-hydroxy-16 alpha-methyl-3-oxoandrosta-1,4-diene 17 beta-thiocarboxylate;

methyl 17 alpha-acetoxy-6 alpha, 9 alpha-difluoro-11 beta-hydroxy-16 alpha-methylandrosta-1,4-diene 17 beta-thiocarboxylate; and the like.

EXAMPLE 3

By following in principle the procedures set forth in Examples 1–2 but substituting the corresponding 16 beta-methyl steroid starting material for the 16 alpha-methyl steroid starting material, the corresponding 16 beta-methyl steroids of this invention are obtained such as methyl 6 alpha, 9 alpha-difluoro-11 beta,17 alpha-dihydroxy-16 beta-methyl-3-oxoandrosta-1,4-diene 17 beta-thiocarboxylate and the corresponding 17 alpha-alkanoyloxy derivatives along with other alkyl, phenyl or benzyl 17 beta-thiocarboxylates.

EXAMPLE 4

By following in principle the procedures set forth in Examples 1-2 but substituting the corresponding 16-unsubstituted steroid starting material for the 16 alpha-methyl steroid starting material, the corresponding 16-unsubstituted steroids of this invention are obtained, such as methyl 6 alpha,9 alpha-difluoro-11 beta,17 alpha-dihydroxy-3-oxoandrosta-1,4-diene 17 beta-thiocarboxylate and other corresponding alkyl, phenyl or benzyl 17 beta-thiocarboxylates as well as the 17-alpha-alkanoyloxy derivatives.

EXAMPLE 5

A process is set forth for preparing alkyl, benzyl or phenyl 16 alpha, 17 alpha-isopropylidenedioxy-3-oxoandrosta-1,4-diene 17 beta-thiocarboxylates of this invention which are substituted with hydrogen, fluoro or chloro at the 6 alpha-position; with hydrogen, fluoro, chloro or bromo at the 9 alpha-position; and with hydroxy at the 11 beta-position or also chloro at the 11 beta-position when there is a chloro at the 9 alpha position.

A. Preparation of methyl 6 alpha, 9 alpha-difluoro-11 beta-hydroxy-16 alpha, 17 alpha-isopropylidenedioxy-3-oxoandrosta-1,4-diene 17 beta-thiocarboxylate.

Six hundred (600) mg of 6 alpha-difluoro-11 beta-hydroxy-16 alpha, 17 alpha, isopropylidenedioxy-3-oxoandrosta-1,4-diene 17 beta-carboxylic acid (prepared in the manner described in Preparation 2, Part A) are mixed with 8 ml/THF and 0.21 ml TEA and stirred under nitrogen at room temperature. Three-tenths (0.3) of a ml of DCP in 11 ml THF is added to the steroid mixture over 6 minutes and the mixture is stirred at room temperature for about 17 hours, at which point, 5 drops of neat DCP are added. Stirring is continued for another 3.5, hours after which the precipitate in the reaction mixture is filtered and washed with 10 ml of THF. The filtrates are combined, and 3.15 ml of the solution of the methyl sulfide, sodium hydride, DMF as prepared in Example 1 is added thereto. The resulting mixture is stirred at room temperature under nitrogen for about 3.5 hours then poured into 300 ml of EtOAc which is then washed twice with 250 ml portions of water. The aqueous washes are extracted with 150 ml EtOAc, and the EtOAc solutions are combined, washed with brine and dried over sodium sulfate for about 15 hours in a refrigerator. The solvents are removed under reduced pressure by rotary evaporator to yield 546 mg of material which is recrystallized from acetone to give 309 mg of methyl 6 alpha, 9 alpha-difluoro-11 beta-hydroxy-16 alpha, 17 alpha-isopropylidenedioxy-3-oxoandrosta-1,4-diene 17 beta-thiocarboxylate, mp 299°-301° C. (with decomposition).

B. Similarly, by substituting other alkyl, phenyl or benzyl sulfides for methyl sulfide, and following in principle the process of Part A of this example, other compounds of this invention are prepared, such as ethyl 6 alpha, 9 alpha-difluoro-11 beta-hydroxy-16 alpha, 17 alpha-isopropylidenedioxy-3-oxoandrosta-1,4-diene 17 beta thiocarboxylate;

isopropyl 6 alpha, 9 alpha-difluoro-11 beta-hydroxy-16 alpha, 17 alpha-isopropylidenedioxy-3-oxoandrosta-1,4-diene 17 beta thiocarboxylate;

n-butyl 6 alpha, 9 alpha-difluoro-11 beta-hydroxy-16 alpha, 17 alpha-isopropylidenedioxy-3-oxoandrosta-1,4-diene 17 beta thiocarboxylate;

n-hexyl 6 alpha, 9 alpha-difluoro-11 beta-hydroxy-16 alpha, 17 alpha-isopropylidenedioxy-3-oxoandrosta-1,4-diene 17 beta thiocarboxylate;

phenyl 6 alpha, 9 alpha-difluoro-11 beta-hydroxy-16 alpha, 17 alpha-isopropylidenedioxy-3-oxoandrosta-1,4-diene 17 beta thiocarboxylate;

benzyl 6 alpha, 9 alpha-difluoro-11 beta-hydroxy-16 alpha, 17 alpha-isopropylidenedioxy-3-oxoandrosta-1,4-diene 17 beta thiocarboxylate; and the like.

C. Similarly by following in principle the procedure of Parts A and B of this example, but substituting other 17 beta-carboxylic acids prepared in the manner set forth in Preparation 2 for 6 alpha, 9 alpha-difluoro-11 beta-hydroxy-16 alpha, 17 alpha-isopropylidenedioxy-3-oxoandrosta-1,4-diene 17 beta-carboxylic acid, other compounds of this invention are prepared, such as methyl 6 alpha-fluoro-11 beta hydroxy-16 alpha, 17 alpha-isopropylidenedioxy-3-oxoandrosta-1,4-diene 17 beta-thiocarboxylate;

methyl 9 alpha fluoro-11 beta hydroxy-16 alpha, 17 alpha-isopropylidenedioxy-3-oxoandrosta-1,4-diene 17 beta-thiocarboxylate;

methyl 9 alpha chloro-11 beta hydroxy-16 alpha, 17 alpha-isopropylidenedioxy-3-oxoandrosta-1,4-diene 17 beta-thiocarboxylate;

methyl 9 alpha chloro-6 alpha-fluoro-11 beta hydroxy-16 alpha, 17 alpha-isopropylidenedioxy-3-oxoandrosta-1,4-diene 17 beta-thiocarboxylate;

methyl 9 alpha bromo-6 alpha-fluoro-11 beta hydroxy-16 alpha, 17 alpha-isopropylidenedioxy-3-oxoandrosta-1,4-diene 17 beta-thiocarboxylate;

methyl 9 alpha, 11 beta-dichloro-6 alpha-fluoro-16 alpha, 17 alpha-isopropylidenedioxy-3-oxoandrosta-1,4-diene 17 beta-thiocarboxylate;

n-butyl 9 alpha,11 beta-dichloro-6 alpha-fluoro-16 alpha, 17 alpha-isopropylidenedioxy-3-oxoandrosta-1,4-diene 17 beta-thiocarboxylate;

phenyl 9 alpha, 11 beta-dichloro-6 alpha-fluoro-16 alpha, 17 alpha-isopropylidenedioxy-3-oxoandrosta-1,4-diene 17 beta-thiocarboxylate;

benzyl 9 alpha, 11 beta-dichloro-6 alpha-fluoro-16 alpha, 17 alpha-isopropylidenedioxy-3-oxoandrosta-1,4-diene 17 beta-thiocarboxylate; and the like.

EXAMPLE 6

This example sets forth a process for preparing an 11-keto compound of this invention by oxidizing any of the 11 beta-hydroxy steroids set forth in Preparations 1-2 and converting the so-obtained compound to the 17 beta-thiocarboxylate according to the process of Examples 1-5.

One g of 6 alpha,9 alpha-difluoro-11 beta,17 alpha-dihydroxy-16 alpha-methyl-3-oxoandrosta-1,4-diene-17 beta-carboxylic acid is dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 6 alpha,9 alpha-difluoro-17 alpha-hydroxy-16 alpha-methyl-3,11-dioxoandrosta-1,4-diene-17 beta-carboxylic acid. This compound, in turn, is reacted according to the process of Example 2 to give methyl 6 alpha, 9 alpha-difluoro-17 alpha-hydroxy-11-keto-16 alpha-methyl-3-oxoandrosta-1,4-diene 17 beta-thiocarboxylate.

EXAMPLE 7

This example sets forth a process for converting an androsta-1,4-diene of this invention to the corresponding androst-4-ene.

To a solution of 25 mg of tris-(triphenylphosphine)-chlororhodium in 7 ml of benzene and 15 ml of ethanol, 244 mg methyl 6 alpha,9 alpha-difluoro-11 beta,17 alpha-dihydroxy-16 alpha-methyl-3-oxoandrosta-1,4-diene 17-thiocarboxylate are added and the resulting solution is stirred under hydrogen at room temperature at atmospheric pressure. After hydrogen uptake is complete the solution is evaporated to dryness and the residue is taken up in a mixture of petroleum ether and methylene chloride. The pure product is isolated by column chromatography on silica gel to give methyl 6 alpha,9 alpha-difluoro-11 beta,17 alpha-dihydroxy-16 alpha-methyl-3-oxoandrost-4-ene 17 beta-thiocarboxylate. Similarly, by substituting other androsta-1,4-dienes of this invention made according to examples 1-6 for the compound used above in this example, other corresponding androsta-4-enes of the invention are prepared.

The subject matter claimed is:

1. A compound chosen from those represented by the formula

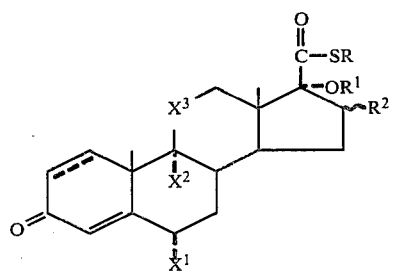

wherein
 $X^1$ is hydrogen, fluoro or chloro;
 $X^2$ is hydrogen, fluoro, chloro or bromo;
 $X^3$ is =C=O or

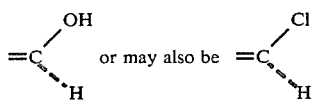

when $X^2$ is chloro;
R is alkyl of 1 through 6 carbon atoms or is phenyl or benzyl optionally substituted with one substituent on the phenyl ring chosen from the group consisting of alkyl of 1 through 4 carbon atoms, alkoxy of 1 through 4 carbon atoms and halo;
$R^1$ is hydrogen or alkanoyl of 2 through 6 carbon atom when $R^2$ is hydrogen, alpha-methyl or beta-methyl;
$OR^1$ and $R^2$ together are 16 alpha, 17 alpha-isopropylidenedioxy; and there is a double or a single bond between C-1 and C-2.

2. The compound of claim 1 wherein $R^2$ is alpha-methyl.

3. The compound of claim 2 wherein R is alkyl of 1 through 6 carbon atoms, phenyl or benzyl and $R^1$ is alkanoyl of 2 through 6 carbon atoms; $X^1$ is fluoro or hydrogen; $X^2$ is hydrogen, fluoro or chloro; and $X^3$ is

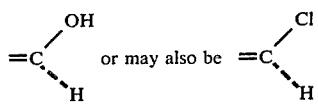

when $X^2$ is chloro.

4. The compound of claim 3 wherein R is alkyl of 1 or 2 carbon atoms.

5. The compound of claim 4 wherein R is methyl; $X^1$ is fluoro; $X^2$ is fluoro or chloro; and $X^3$ is

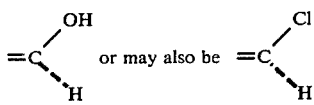

when $X^1$ is chloro.

6. The compound of claim 5 wherein $X^1$ and $X^2$ are fluoro and $X^3$ is

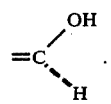

7. The compound of claim 6 wherein the bond between C-1 and C-2 is a double bond, $X^1$ and $X^2$ are both fluoro, R is methyl and $R^1$ is hydrogen, namely methyl 6 alpha,9 alpha-difluoro-11 beta,17 alpha-dihydroxy-16 alpha-methyl-3-oxoandrosta-1,4-diene 17 beta-thiocarboxylate.

8. The compound of claim 6 wherein the bond between C-1 and C-2 is a double bond, $X^1$ and $X^2$ are both fluoro, $X^3$ is

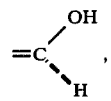

R is methyl and $R^1$ is propionyl, namely methyl 6 alpha,9alpha-difluoro-11 betahydroxy-16 alpha-methyl-3-oxo-17 alpha-propionyloxyandrosta-1,4-diene 17 beta-thiocarboxylate.

9. The compound of claim 4 wherein $X^1$ and $X^2$ are both fluoro, $X^3$ is

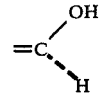

R is ethyl and $R^1$ is hydrogen, namely ethyl 6 alpha, 9 alpha-difluoro-11 beta, 17 alpha-dihydroxy-16 alpha-methyl-3-oxoandrosta-1,4-diene 17 beta-thiocarboxylate.

10. The compound of claim 4 wherein $X^1$ and $X^2$ are both fluoro, $X^3$ is

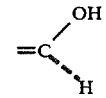

R is isopropyl and R¹ is propionyl, namely ethyl 6 alpha, 9 alpha-difluoro-11 beta-hydroxy-16 alpha-methyl-3-oxo-17 alpha-propionyloxyandrosta-1,4-diene 17 beta-thiocarboxylate.

11. The compound of claim 3 wherein X¹ and X² are both fluoro, X³ is

R is isopropyl and R¹ is propionyl, namely isopropyl 6 alpha, 9 alpha-difluoro-11 beta-hydroxy-16 alpha-methyl-3-oxo-17 alpha-propionyloxyandrosta-1,4-diene 17 beta-thiocarboxylate.

12. The compound of claim 3 wherein X¹ and X² are both fluoro, X³ is

R is n-butyl and R¹ is propionyl, namely n-butyl 6 alpha, 9 alpha-difluoro-11 beta-hydroxy-16 alpha-methyl-3-oxo-17 alpha-propionyloxyandrosta-1,4-diene 17 beta-thiocarboxylate.

13. The compound of claim 3 wherein X¹ and X² are both fluoro, X³ is

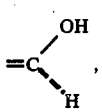

R is phenyl and R¹ is propionyl, namely phenyl 6 alpha, 9 alpha-difluoro-11 beta-hydroxy-16 alpha-methyl-3-oxo-17 alpha-propionyloxyandrosta-1,4-diene 17 beta-thiocarboxylate.

14. The compound of claim 3 wherein X¹ and X² are both fluoro, X³ is

R is benzyl and R¹ is propionyl, namely benzyl 6 alpha, 9 alpha-difluoro-11 beta-hydroxy-16 alpha-methyl-3-oxo-17 alpha-propionyloxyandrosta-1,4-diene 17 beta-thiocarboxylate.

15. The compound of claim 5 wherein X² is chloro and X³ is

16. The compound of claim 15 wherein the bond between C-1 and C-2 is a double bond, R is methyl and R¹ is propionyl, namely methyl 9 alpha, 11 beta-dichloro-6 alpha-fluoro-16 alpha-methyl-3-oxo 17 alpha-propionyloxyandrosta-1,4-diene 17 beta-thiocarboxylate.

17. A compound of claim 1 wherein

R is alkyl of one through six carbon atoms, benzyl or phenyl;
OR¹ and R² together are 16 alpha,17 alpha-isopropylidenedioxy;
X¹ is fluoro;
X² is hydrogen, fluoro or chloro; and
X³ is

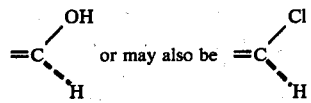

when X² is chloro.

18. A compound of claim 17 wherein R is methyl or ethyl.

19. A compound of claim 18 wherein R is methyl and X² is fluoro or chloro.

20. A compound of claim 19 wherein there is a double bond between C-1 and C-2, X² is fluoro and X³ is

namely methyl 6 alpha,9 alpha-difluoro-11 beta hydroxy-16 alpha,17 alpha-isopropylidenedioxyandrosta-1,4-diene 17 beta-thiocarboxylate.

21. A compound of claim 19 wherein there is a double bond between C-1 and C-2, X² is chloro and X³ is

namely methyl 9 alpha,11 beta-dichloro-6 alpha fluoro-16 alpha,17 alpha-isopropylidenedioxy-3-oxoandrosta-1,4-diene 17 beta-thiocarboxylate.

22. An anti-inflammatory pharmaceutical composition which comprises a suitable pharmaceutical excipient in combination with the compound of claim 1 in an amount sufficient to effect an anti-inflammatory response when administered to a mammal having need thereof.

23. An anti-inflammatory pharmaceutical composition which comprises a suitable pharmaceutical excipient in combination with the compound of claim 2 in an amount sufficient to effect an anti-inflammatory response when administered to a mammal having need thereof.

24. An anti-inflammatory pharmaceutical composition which comprises a suitable pharmaceutical excipient in combination with the compound of claim 3 in an amount sufficient to effect an anti-inflammatory response when administered to a mammal having need thereof.

25. An anti-inflammatory pharmaceutical composition which comprises a suitable pharmaceutical excipient in combination with the compound of claim 4 in an amount sufficient to effect an anti-inflammatory response when administered to a mammal having need thereof.

26. An anti-inflammatory pharmaceutical composition which comprises a suitable pharmaceutical excipient in combination with the compound of claim 5 in an amount sufficient to effect an anti-inflammatory response when administered to a mammal having need thereof.

27. An anti-inflammatory pharmaceutical composition which comprises a suitable pharmaceutical excipient in combination with the compound of claim 17 in an amount sufficient to effect an anti-inflammatory response when administered to a mammal having need thereof.

28. An anti-inflammatory pharmaceutical composition which comprises a suitable pharmaceutical excipient in combination with the compound of claim 18 in an amount sufficient to effect an anti-inflammatory response when administered to a mammal having need thereof.

29. A method for treating an inflamed condition in a mammal which comprises administering the compound of claim 1 to said mammal in an amount sufficient to effect an anti-inflammatory response in said mammal.

30. A method for treating an inflamed condition in a mammal which comprises administering the compound of claim 2 to said mammal in an amount sufficient to effect an anti-inflammatory response in said mammal.

31. A method for treating an inflamed condition in a mammal which comprises administering the compound of claim 3 to said mammal in an amount sufficient to effect an anti-inflammatory response in said mammal.

32. A method for treating an inflamed condition in a mammal which comprises administering the compound of claim 4 to said mammal in an amount sufficient to effect an anti-inflammatory response in said mammal.

33. A method for treating an inflamed condition in a mammal which comprises administering the compound of claim 5 to said mammal in an amount sufficient to effect an anti-inflammatory response in said mammal.

34. A method for treating an inflamed condition in a mammal which comprises administering the compound of claim 17 to said mammal in an amount sufficient to effect an anti-inflammatory response in said mammal.

35. A method for treating an inflamed condition in a mammal which comprises administering the compound of claim 18 to said mammal in an amount sufficient to effect an anti-inflammatory response in said mammal.

36. The compound of claim 6 wherein the bond between C-1 and C-2 is a double bond, R is methyl and $R^1$ is

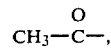

namely methyl 17 alpha-acetoxy-6 alpha,9 alpha-difluoro-11-beta-hydroxy-16 alpha-methylandrosta-1,4-diene 17 beta-thiocarboxylate.

37. The compound of claim 18 wherein $X^1$ and $X^2$ are both fluoro, $X^3$ is

and R is ethyl, namely ethyl 6 alpha, 9 alpha-difluoro-11 beta-hydroxy-16 alpha,17 alpha-isopropylidenedioxyandrosta-1,4-diene 17 beta-thiocarboxylate.

38. The compound of claim 1 wherein $R^2$ is beta methyl.

39. The compound of claim 1 wherein $X^1$ and $X^2$ are each independently hydrogen or fluoro, R is methyl and $R^1$ is alkanoyl of 2–6 carbon atoms.

40. An anti-inflammatory pharmaceutical composition which comprises a suitable pharmaceutical excipient in combination with the compound of claim 38 in an amount sufficient to effect an anti-inflammatory response when administered to a mammal having need thereof.

41. A method for treating an inflamed condition in a mammal which comprises administering the compound of claim 38 to said mammal in an amount sufficient to effect an anti-inflammatory response in said mammal.

* * * * *